US008647838B2

(12) United States Patent
Kiryukhin et al.

(10) Patent No.: US 8,647,838 B2
(45) Date of Patent: Feb. 11, 2014

(54) METHOD FOR PRODUCING L-ARGININE USING A BACTERIUM OF ENTEROBACTERIACEAE FAMILY, HAVING ATTENUATED EXPRESSION OF A GENE ENCODING AN L-ARGININE TRANSPORTER

(75) Inventors: Mikhail Yurievich Kiryukhin, Moscow (RU); Yulia Georgievna Rostova, Moscow (RU); Elvira Borisovna Voroshilova, Moscow (RU); Mikhail Markovich Gusyatiner, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 505 days.

(21) Appl. No.: 12/629,385

(22) Filed: Dec. 2, 2009

(65) Prior Publication Data

US 2010/0143983 A1    Jun. 10, 2010

(30) Foreign Application Priority Data

Dec. 9, 2008 (RU) .............................. 2008148283

(51) Int. Cl.
*C12P 1/00* (2006.01)
(52) U.S. Cl.
USPC .......................................................... 435/41
(58) Field of Classification Search
None
See application file for complete search history.

(56) References Cited

U.S. PATENT DOCUMENTS

| | | | |
|---|---|---|---|
| 4,278,765 A | 7/1981 | Debabov et al. | |
| 4,346,170 A | 8/1982 | Sano et al. | |
| 5,661,012 A | 8/1997 | Sano et al. | |
| 6,040,160 A | 3/2000 | Kojima et al. | |
| 7,138,266 B2 | 11/2006 | Debabov et al. | |
| 7,259,003 B2 | 8/2007 | Livshits et al. | |
| 7,312,058 B2 | 12/2007 | Kashiwagi et al. | |
| 7,381,548 B2 | 6/2008 | Sheremet'eva et al. | |
| 7,422,880 B2 | 9/2008 | Rybak et al. | |
| 7,476,531 B2 | 1/2009 | Tabolina et al. | |
| 7,531,332 B2 | 5/2009 | Livshits et al. | |
| 7,618,803 B2 | 11/2009 | Tabolina et al. | |
| 7,618,804 B2 | 11/2009 | Tabolina et al. | |
| 2005/0214911 A1 | 9/2005 | Marchenko et al. | |
| 2006/0088919 A1 | 4/2006 | Rybak et al. | |
| 2008/0113416 A1 | 5/2008 | Filippov et al. | |
| 2009/0081738 A1 | 3/2009 | Filippov et al. | |
| 2009/0087886 A1 | 4/2009 | Filippov et al. | |
| 2009/0098621 A1 | 4/2009 | Rybak et al. | |
| 2009/0117623 A1 | 5/2009 | Marchenko et al. | |
| 2009/0137011 A1 | 5/2009 | Filippov et al. | |
| 2009/0170169 A1 | 7/2009 | Filippov et al. | |
| 2009/0215129 A1 | 8/2009 | Rybak et al. | |
| 2009/0226980 A1 | 9/2009 | Filippov et al. | |
| 2009/0239267 A1 | 9/2009 | Rybak et al. | |
| 2009/0269819 A1 | 10/2009 | Filippov et al. | |

FOREIGN PATENT DOCUMENTS

| | | |
|---|---|---|
| EP | 1829965 | 9/2007 |
| WO | WO95/16042 | 6/1995 |
| WO | WO2007/013639 | 2/2007 |

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Rajagopal et al, Use of Inducible Feedback-Resistant N-Acetylglutamate Synthetase (argA) Genes for Enhanced Arginine Biosynthesis by Genetically Engineered *Escherichia coli* K-12 Strains. Applied and Environmental Microbiology vol. 64, 1998, p. 1805-1811.*
Utagawa et al, Production of arginine by fermentation. J Nutr. Oct. 2004;134(10 Suppl):2854S-2857S.*
Caldara, M., et al., "The arginine regulon of *Escherichia coli*: whole-system transcriptome analysis discovers new genes and provides an integrated view of arginine regulation," Microbiol. 2006;152:3343-3354.
Wissenbach, U., et al., "A third periplasmic transport system for L-arginine in *Escherichia coli*: molecular characterization of the *artPIQMJ* genes, arginine binding and transport," Mol. Microbiol. 1995;17(4):675-686.
Siak-Wei Ow, S., et al. "Global transcriptional analysis of metabolic burden due to plasmid maintenance in *Escherichia coli* DH5α during batch fermentation," Enzyme Microbiol. Technol. 2006;39(3):391-398.
Xie, Y., et al., "Transcriptome of *Escherichia coli* K1 bound to human brain microvascular endothelial cells," Biochem. Biophys. Res. Comm. 2008;365:201-206.
European Search Report for EP Patent App. No. 09015195.2 (Mar. 24, 2010).
Office Action from Chinese Patent App. No. 200910225200.6 (Jul. 4, 2012).

* cited by examiner

*Primary Examiner* — Sheridan Swope
(74) *Attorney, Agent, or Firm* — Shelly Guest Cermak; Cermak Nakajima LLP

(57) ABSTRACT

The present invention provides a method for producing L-arginine using a bacterium of the Enterobacteriaceae family, particularly a bacterium belonging to the genus *Escherichia* or *Pantoea*, which has been modified to attenuate expression of one or several genes encoding an L-arginine transporter.

1 Claim, 2 Drawing Sheets

US 8,647,838 B2

METHOD FOR PRODUCING L-ARGININE USING A BACTERIUM OF ENTEROBACTERIACEAE FAMILY, HAVING ATTENUATED EXPRESSION OF A GENE ENCODING AN L-ARGININE TRANSPORTER

This application claims priority under 35 U.S.C. §119 to Russian Patent Application No. 2008148283, filed on Dec. 9, 2008, which is incorporated in its entirety by reference. The Sequence Listing in electronic format filed herewith is also hereby incorporated by reference in its entirety (File Name: US-419_Seq_List; File Size: 30 KB; Date Created: Dec. 2, 2009).

BACKGROUND OF THE INVENTION

1. Field of the Invention

The present invention relates to the microbiological industry, and specifically to a method for producing L-arginine. The method uses a bacterium of the Enterobacteriaceae family which has been modified to attenuate expression of one or several genes encoding an L-arginine transporter.

2. Description of the Related Art

Conventionally, L-amino acids are industrially produced by fermentation methods utilizing strains of microorganisms from natural sources, or mutants thereof. Typically, the microorganisms are modified to enhance production yields of target L-amino acids.

Many techniques to enhance L-amino acid production yields have been reported, including by transforming microorganisms with recombinant DNA (see, for example, U.S. Pat. No. 4,278,765). Other techniques for enhancing production yields include increasing the activities of enzymes involved in amino acid biosynthesis and/or desensitizing the target enzymes of the feedback inhibition caused by the produced L-amino acid (see, for example, WO 95/16042 or U.S. Pat. Nos. 4,346,170; 5,661,012 and 6,040,160).

Other ways to enhance L-amino acid production yields is to attenuate expression of a gene or several genes which are involved in the degradation of the target L-amino acid, genes which divert the precursors of the target L-amino acid from the L-amino acid biosynthetic pathway, genes involved in the redistribution of the carbon, nitrogen, and phosphate fluxes, and genes coding for toxins, etc.

A transport system dependent on a binding protein in *Escherichia coli* specific for L-arginine was characterized by genetic and biochemical means. The system is made up of five adjacent genes, artPIQMJ ("art" stands for arginine transport), which are organized in two transcriptional units (artPIQM and artJ). The artI and artJ gene products, ArtI and ArtJ, are periplasmic binding proteins with sequence similarity to binding proteins for polar, or basic amino acids. The artQ, artM, and artP products are similar to known transmembrane proteins and the ATPase of binding-protein-dependent carriers. The mature ArtI and ArtJ proteins are localized in the periplasm and lack a signal peptide of 19 amino acid residues. ArtI and ArtJ were isolated from overproducing strains. ArtJ specifically binds L-arginine with high affinity and overproduction of ArtJ stimulated L-arginine uptake by bacteria. The substrate for ArtI is not known, and isolated ArtI did not bind common amino acids, various basic uncommon amino acids, or amines. It was concluded that the artPIQM artJ genes encode a third arginine-uptake system in addition to the known argT hisJQMP system of *Salmonella typhimurium* and *E. coli* and the arginine (-ornithine) carrier (aps) of *E. coli* (Wissenbach U. et al., Mol Microbiol.; 17(4):675-86 (1995)).

But currently, there have been no reports of attenuating expression of a gene encoding an L-arginine transporter for production of L-arginine.

SUMMARY OF THE INVENTION

An aspect of the present invention includes enhancing the productivity of L-arginine producing strains and providing a method for producing L-arginine acid using these strains.

The present invention provides a bacterium of the Enterobacteriaceae family having an increased ability to produce L-arginine.

It is an aspect of the present invention to provide an L-arginine producing bacterium of the Enterobacteriaceae family, wherein the bacterium has been modified to attenuate expression of one or several genes encoding an L-arginine transporter.

It is a further aspect of the present invention to provide the bacterium as described above, wherein said bacterium has been modified to attenuate expression of artI gene.

It is a further aspect of the present invention to provide the bacterium as described above, wherein expression of the artI gene is attenuated by inactivation of the artI gene.

It is a further aspect of the present invention to provide the bacterium as described above, wherein said bacterium has been modified to attenuate expression of artPIQM-artJ cluster.

It is a further aspect of the present invention to provide the bacterium as described above, wherein expression of the artPIQM-artJ cluster is attenuated by inactivation of the artPIQM-artJ cluster.

It is a further aspect of the present invention to provide the bacterium as described above, wherein the bacterium belongs to the genus *Escherichia*.

It is a further aspect of the present invention to provide the bacterium as described above, wherein the bacterium belongs to the genus *Pantoea*.

It is a further aspect of the present invention to provide a method for producing L-arginine comprising:
cultivating the bacterium as described above, and
collecting L-arginine from the medium.

The present invention is described in detail below.

DETAILED DESCRIPTION OF EXEMPLARY EMBODIMENTS

1. Bacterium

Figure 1:
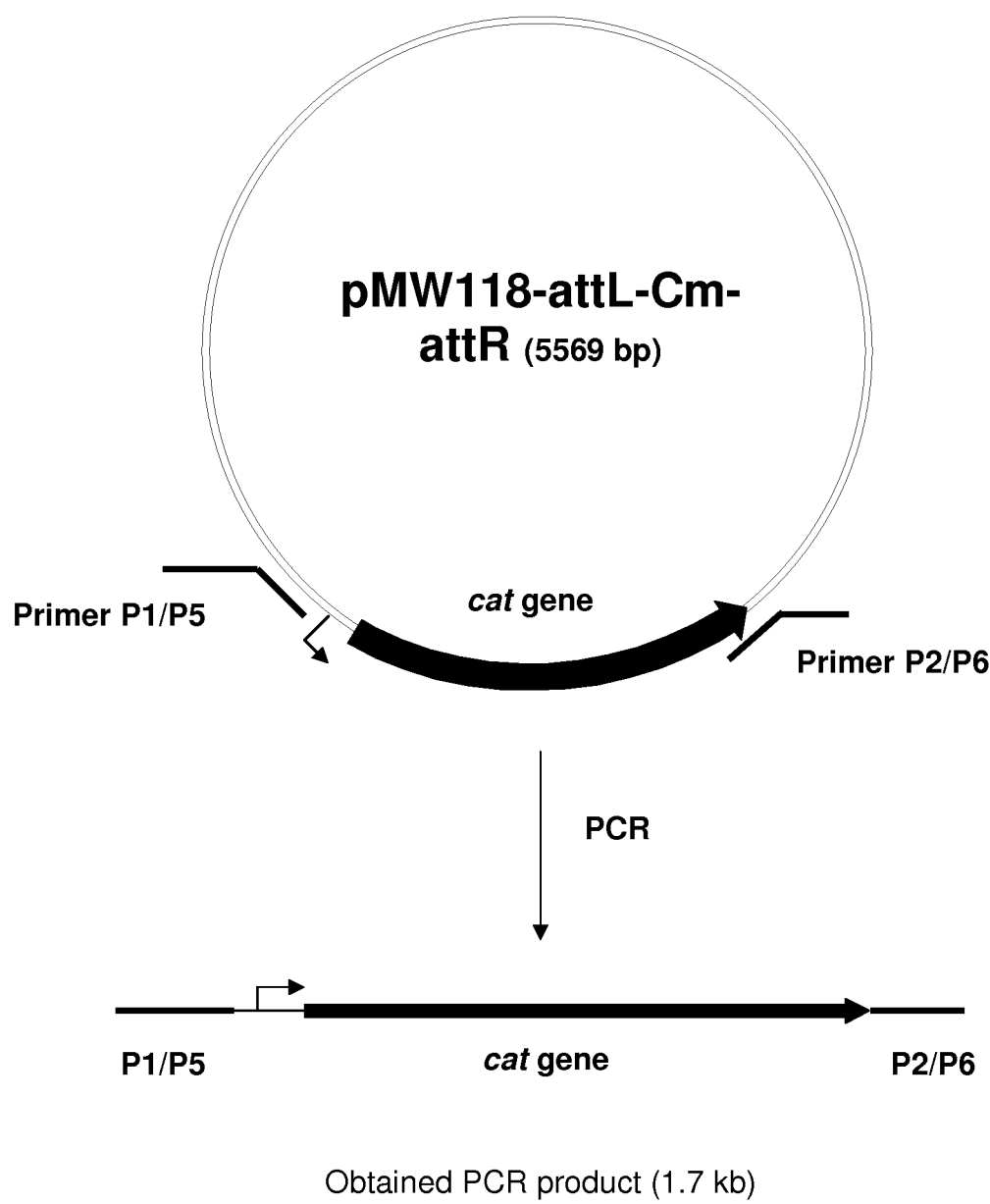
FIG. 1 shows the relative positions of pairs of the primers P1 and P2, and P5 and P6 on plasmid pMW118-attL-Cm-attR.

The bacterium is an L-arginine producing bacterium of the Enterobacteriaceae family, wherein the bacterium can be modified to attenuate expression of one or several genes encoding an L-arginine transporter.

The term "L-arginine producing bacterium" can mean a bacterium which is able to produce and secrete L-arginine into a medium, when the bacterium is cultured in the medium.

The term "L-arginine-producing bacterium" also can mean a bacterium which is able to produce and cause accumulation of L-arginine in a culture medium in an amount larger than a wild-type or parental strain of a bacterium of the Enterobacteriaceae family, for example, *E. coli*, such as *E. coli* K-12, and can also mean that the bacterium is able to cause accumulation in a medium of an amount not less than 0.5 g/L, or in another example, not less than 1.0 g/L of L-arginine.

The Enterobacteriaceae family includes bacteria belonging to the genera *Escherichia, Enterobacter, Erwinia, Klebsiella, Pantoea, Photorhabdus, Providencia, Salmonella, Serratia, Shigella, Morganella* and *Yersinia*, etc. Specifically, those classified as Enterobacteriaceae according to the taxonomy used in the NCBI (National Center for Biotechnology Information) database www.ncbi.nlm.nih.gov/Taxonomy/Browser/wwwtax.cgi?id=91347) can be used. A bacterium belonging to the genus *Escherichia* or *Pantoea* can also be used.

The phrase "a bacterium belonging to the genus *Escherichia*" can mean that the bacterium is classified in the genus *Escherichia* according to the classification known to a person skilled in the art of microbiology. An example of a bacterium belonging to the genus *Escherichia* can be, but is not limited to, *Escherichia coli* (*E. coli*).

The bacterium belonging to the genus *Escherichia* is not particularly limited, however for example, bacteria described by Neidhardt, F. C. et al. (*Escherichia coli* and *Salmonella typhimurium*, American Society for Microbiology, Washington D.C., 1208, Table 1) are encompassed.

The phrase "a bacterium belonging to the genus *Pantoea*" can mean that the bacterium is classified as the genus *Pantoea* according to the classification known to a person skilled in the art of microbiology. Some species of *Enterobacter agglomerans* have been recently re-classified into *Pantoea agglomerans, Pantoea ananatis, Pantoea stewartii* or the like, based on nucleotide sequence analysis of 16S rRNA, etc.

The phrase "bacterium has been modified to attenuate expression of one or several genes encoding an L-arginine transporter" can mean that the bacterium has been modified in such a way that the modified bacterium contains a reduced amount of the L-arginine transporter or any subunit thereof as compared with an unmodified bacterium, or it can also mean that the bacterium is unable to synthesize the L-arginine transporter or any subunit thereof.

The L-arginine transporter system is made up of products of five adjacent genes, artPIQMJ, which are organized into two transcriptional units, artPIQM and artJ. The artI and artJ gene products, ArtI and ArtJ, are periplasmic binding proteins with sequence similarity to binding proteins for polar, or basic amino acids. The artQ, artM, and artP products are similar to known transmembrane proteins and the ATPase of binding-protein-dependent carriers.

The phrase "inactivation of a gene" can mean that the modified gene encodes a completely non-functional protein. It is also possible that the modified DNA region is unable to naturally express the gene due to the deletion of a part of the gene or the gene entirely, a shifting of the reading frame of the gene, the introduction of missense/nonsense mutation(s), or the modification of an adjacent region of the gene, including the sequences controlling gene expression, such as the promoter, enhancer, attenuator, ribosome-binding site, etc.

The presence or absence of a gene on the chromosome of a bacterium can be detected by well-known methods, including PCR, Southern blotting, and the like. In addition, the level of gene expression can be estimated by measuring the amount of mRNA transcribed from the gene using various well-known methods, including Northern blotting, quantitative RT-PCR, and the like. The amount of the protein encoded by the gene can be measured by well-known methods, including SDS-PAGE followed by an immunoblotting assay (Western blotting analysis), and the like.

The artP gene (synonyms: ECK0855, b0864) encodes the ArtP protein subunit of the arginine ABC transporter (synonym B0864) located in the cytoplasm. The artP gene (nucleotides complementary to nucleotides 902,229 to 902,957 in the GenBank accession number NC_000913.2; gi:49175990; SEQ ID NO: 1) is located between the ybjP and artI genes on the chromosome of *E. coli* K-12 strain. The nucleotide sequence of the artP gene, and the amino acid sequence of ArtP protein encoded by the artP gene, are shown in SEQ ID NO: 1 and SEQ ID NO: 2, respectively.

The artI gene (synonyms: ECK0854, b0863) encodes the ArtI protein subunit of the arginine ABC transporter (synonym B0863) located in the periplasmic space. The artI gene (nucleotides complementary to nucleotides 901,480 to 902,211 in the GenBank accession number NC_000913.2; gi:49175990; SEQ ID NO: 3) is located between the artQ and artP genes on the chromosome of *E. coli* K-12 strain. The nucleotide sequence of the artI gene, and the amino acid sequence of ArtI protein encoded by the artI gene, are shown in SEQ ID NO: 3 and SEQ ID NO: 4, respectively.

The artQ gene (synonyms: ECK0853, b0862) encodes the ArtQ protein subunit of the arginine ABC transporter (synonym B0862) located in the inner membrane. The artQ gene (nucleotides complementary to nucleotides 900,757 to 901,473 in the GenBank accession number NC_000913.2; gi:49175990; SEQ ID NO: 5) is located between the artI and artM genes on the chromosome of *E. coli* K-12 strain. The nucleotide sequence of the artQ gene, and the amino acid sequence of ArtQ protein encoded by the artI gene, are shown in SEQ ID NO: 5 and SEQ ID NO: 6, respectively.

The artM gene (synonyms: ECK0852, b0861) encodes the ArtM protein subunit of the arginine ABC transporter (synonym B0861) located in the inner membrane. The artI gene (nucleotides complementary to nucleotides 900,089 to 900,757 in the GenBank accession number NC_000913.2; gi:49175990; SEQ ID NO: 7) is located between the artQ and artJ genes on the chromosome of *E. coli* K-12 strain. The nucleotide sequence of the artM gene, and the amino acid sequence of ArtM protein encoded by the artM gene, are shown in SEQ ID NO: 7 and SEQ ID NO: 8, respectively.

The artJ gene (synonyms: ECK0851, b0860) encodes the ArtJ protein subunit of the arginine ABC transporter (synonym B0860) located in the periplasmic space. The artJ gene (nucleotides complementary to nucleotides 899,067 to 899,798 in the GenBank accession number NC_000913.2; gi:49175990; SEQ ID NO: 9) is located between the artM and rlmC genes on the chromosome of *E. coli* K-12 strain. The nucleotide sequence of the artJ gene, and the amino acid sequence of ArtJ protein encoded by the artJ gene, are shown in SEQ ID NO: 9 and SEQ ID NO: 10, respectively.

Since there may be some differences in DNA sequences between the genera or strains of the Enterobacteriaceae family, the gene to be inactivated on the chromosome is not limited to the genes shown in SEQ ID NOs:1, 3, 5, 7 or 9, but may include genes homologous to SEQ ID Nos:1, 3, 5, 7 and 9, and which encode a variant protein of corresponding protein. The phrase "variant protein" means a protein which has changes in the sequence, whether they are deletions, insertions, additions, or substitutions of amino acids, but still maintains the activity of the product as the protein.

The number of changes in the variant protein depends on the position in the three dimensional structure of the protein or the type of amino acid residues. It may be 1 to 30, preferably 1 to 15, and more preferably 1 to 5. These changes in the variants are conservative mutations that preserve the function of the protein. In other words, these changes in the variants can occur in regions of the protein which are not critical for the function of the protein. This is because some amino acids have high homology to one another so the three dimensional structure or activity is not affected by such a change. A conservative mutation is a mutation wherein substitution takes place mutually among Phe, Trp, Tyr, if the substitution site is an aromatic amino acid; among Leu, Ile, Val, if the substitution site is a hydrophobic amino acid; between Gln, Asn, if it is a polar amino acid; among Lys, Arg, His, if it is a basic amino acid; between Asp, Glu, if it is an acidic amino acid; and between Ser, Thr, if it is an amino acid having a hydroxyl group. Typical conservative mutations are conservative substitutions. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. Substitutions, deletions, insertions, additions, or inversions and the like of the amino acids described above include naturally occurring mutations (mutant or variant) depending on differences in species, or individual differences of microorganisms that retain the artI gene. Such a gene can be obtained by modifying the nucleotide sequence shown in SEQ ID NO: 1 using, for example, site-directed mutagenesis, so that the site-specific amino acid residue in the protein encoded includes substitutions, deletions, insertions, or additions. The protein variant encoded by the gene may have a homology of not less than 80%, and in another example, not less than 90%, and in another example, not less than 95%, with respect to the entire amino acid sequence shown in SEQ ID NO. 2, 4, 6, 8 or 10 as long as the protein prior to inactivation is able to function as an arginine ABC transporter when complexed with the rest of 4 subunits of 5 wild-type proteins which compose the L-arginine transporter.

Homology between two amino acid sequences can be determined using well-known methods, for example, the computer program BLAST 2.0, which calculates three parameters: score, identity, and similarity.

Moreover, any of the artP, artI, artQ, artM or artJ genes may be a variant which hybridizes with the nucleotide sequence complementary to the sequence shown in SEQ ID NO:1, 3, 5, 7 or 9, respectively, or a probe which can be prepared from the nucleotide sequence, under stringent conditions, provided that it encodes a functional protein prior to inactivation. "Stringent conditions" include those under which a specific hybrid, for example, a hybrid having homology of not less than 60%, and in another example, not less than 70%, an in another example, not less than 80%, and in another example, not less than 90%, and in yet another example not less than 95%, is formed and a non-specific hybrid, for example, a hybrid having homology lower than the above, is not formed. For example, stringent conditions are exemplified by washing one time, and in another example two or three times at a salt concentration corresponding to 1×SSC, 0.1% SDS, and in another example 0.1×SSC, 0.1% SDS at 60° C. Duration of washing depends on the type of membrane used for blotting and, as a rule, may be what is recommended by the manufacturer. For example, the recommended duration of washing for the Hybond™ N+ nylon membrane (Amersham) under stringent conditions is 15 minutes. Preferably, washing may be performed 2 to 3 times. The length of the probe may be suitably selected depending on the hybridization conditions, and is usually 100 by to 1 kbp.

Expression of a gene can be attenuated by introducing a mutation into the gene on the chromosome so that the intracellular activity of the protein encoded by the gene is decreased as compared with an unmodified strain. Mutations which result in attenuation of expression of the gene include the replacement of one base or more to cause an amino acid substitution in the protein encoded by the gene (missense mutation), introduction of a stop codon (nonsense mutation), deletion or insertion of one or two bases to cause a frame shift, insertion of a drug-resistance gene, or deletion of a part of the gene or the entire gene (Qiu, Z. and Goodman, M. F., J. Biol. Chem., 272, 8611-8617 (1997); Kwon, D. H. et al, J. Antimicrob. Chemother., 46, 793-796 (2000)). Expression of the artI gene can also be attenuated by modifying an expression regulating sequence such as the promoter, the Shine-Dalgarno (SD) sequence, etc. (WO95/34672, Carrier, T. A. and Keasling, J. D., Biotechnol Prog 15, 58-64 (1999)).

For example, the following methods can be employed to introduce a mutation by gene recombination. A mutant gene encoding a mutant protein with decreased activity can be prepared, and the bacterium to be modified can be transformed with a DNA fragment containing the mutant gene. Then, the native gene on the chromosome can be replaced with the mutant gene by homologous recombination, and the resulting strain can be selected. Gene replacement using homologous recombination can be conducted by employing a linear DNA, which is known as "Red-driven integration" (Datsenko, K. A. and Wanner, B. L., Proc. Natl. Acad. Sci. USA, 97, 12, p 6640-6645 (2000)), or by employing a plasmid containing a temperature-sensitive replication origin (U.S. Pat. No. 6,303,383 or JP 05-007491A). Furthermore, site-specific mutation by gene substitution can also be incorporated using homologous recombination such as set forth above using a plasmid which is unable to replicate in the host.

Expression of the gene can also be attenuated by inserting a transposon or an IS factor into the coding region of the gene (U.S. Pat. No. 5,175,107), or by conventional methods, such as by mutagenesis with UV irradiation or nitrosoguanidine (N-methyl-N'-nitro-N-nitrosoguanidine).

The gene can also be inactivated by conventional methods, such as by mutagenesis using UV irradiation or nitrosoguanidine (N-methyl-N'-nitro-N-nitrosoguanidine), site-directed mutagenesis, gene disruption using homologous recombination, or/and insertion-deletion mutagenesis (Yu, D. et al., Proc. Natl. Acad. Sci. USA, 2000, 97:12: 5978-83 and Datsenko, K. A. and Wanner, B. L., Proc. Natl. Acad. Sci. USA, 2000, 97:12: 6640-45), also called "Red-driven integration".

Methods for preparation of plasmid DNA, digestion and ligation of DNA, transformation, selection of oligonucleotides as primers, and the like can be ordinary methods well known to one skilled in the art. These methods are described, for instance, in Sambrook, J., Fritsch, E. F., and Maniatis, T., "Molecular Cloning A Laboratory Manual, Second Edition", Cold Spring Harbor Laboratory Press (1989).

L-Arginine Producing Bacteria

Bacteria which are modified to attenuate expression of one or several genes encoding an L-arginine transporter and which are able to produce L-arginine can be employed.

The bacterium can be obtained by inactivating one or several genes encoding an L-arginine transporter in a bacterium which has a native or inherent ability to produce L-arginine.

Alternatively, the bacterium can be obtained by imparting the ability to produce L-arginine to a bacterium already having an inactivated one or several genes encoding an L-arginine transporter.

Examples of parent strains which can be used to derive L-arginine-producing bacteria include, but are not limited to, strains belonging to the genus *Escherichia*, such as *E. coli* strain 237 (VKPM B-7925) (U.S. Patent Application 2002/058315 A1) and its derivative strains harboring mutant N-acetylglutamate synthase (Russian Patent Application No. 2001112869), *E. coli* strain 382 (VKPM B-7926) (EP1170358A1), an arginine-producing strain into which the argA gene encoding N-acetylglutamate synthetase has been introduced (EP1170361A1), and the like.

Examples of parent strains which can be used to derive L-arginine producing bacteria also include strains in which expression of one or more genes encoding L-arginine biosynthetic enzymes is/are enhanced. Examples of such genes include the genes encoding N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB). The abbreviations in parentheses after the enzyme names represent the gene names.

2. Method of the Present Invention

Exemplary methods include producing L-arginine by cultivating the bacterium as described herein in a culture medium to produce and secrete L-arginine into the medium, and collecting L-arginine from the medium.

The cultivation, collection, and purification of L-arginine from the medium and the like can be performed by conventional fermentation methods wherein an amino acid is produced using a bacterium.

The medium used for the culture can be either a synthetic or natural medium, so long as the medium includes a carbon source and a nitrogen source and minerals and, if necessary, appropriate amounts of nutrients which the chosen bacterium requires for growth. The carbon source may include various carbohydrates such as glucose and sucrose, and various organic acids. Depending on the mode of assimilation of the chosen microorganism, alcohol, including ethanol and glycerol, may be used. As the nitrogen source, various ammonium salts such as ammonia and ammonium sulfate, other nitrogen compounds such as amines, a natural nitrogen source such as peptone, soybean-hydrolysate, and digested fermentative microorganism can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation can be performed under aerobic conditions, such as by a shaking culture, and by a stirring culture with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, 1 to 5-day cultivation leads to accumulation of L-arginine in the liquid medium.

After cultivation, solids such as cells can be removed from the liquid medium by centrifugation or membrane filtration, and then L-arginine can be collected and purified by ion-exchange, concentration, and/or crystallization methods.

EXAMPLES

The present invention will be more concretely explained below with reference to the following non-limiting Examples.

Example 1

Construction of a Strain with an Inactivated artI Gene

1. Deletion of the artI Gene

The artI gene in a bacterial strain was deleted by the method initially developed by Datsenko, K. A. and Wanner, B. L. (Proc. Natl. Acad. Sci. USA, 2000, 97(12), 6640-6645) called "Red-driven integration". According to this procedure, the PCR primers P1 (SEQ ID NO: 11) and P2 (SEQ ID NO: 12), which are homologous to both the region adjacent to the artI gene and the gene which confers antibiotic resistance in the template plasmid, were constructed. The plasmid pMW118-attL-Cm-attR (WO 05/010175) was used as the template in the PCR reaction. Conditions for PCR were as follows: initial DNA denaturation for 5 min at 95° C., followed by 25 cycles of denaturation at 95° C. for 30 sec, annealing at 54° C. for 30 sec, elongation at 72° C. for 40 sec; and the final elongation for 5 min at +72° C.

The 1.7 kb PCR product (FIG. 1) was purified from an agarose gel and used for electroporation of the *E. coli* strain MG1655 (ATCC 700926), which contains the plasmid pKD46. The pKD46 plasmid (Datsenko, K. A. and Wanner, B. L., Proc. Natl. Acad. Sci. USA, 2000, 97:12:6640-45) contains a temperature-sensitive replication origin, and includes a 2,154 nucleotide DNA fragment of phage λ (nucleotide positions 31088 to 33241, GenBank accession no. J02459), as well as the genes of the λ Red homologous recombination system (γ, β, exo genes) which are under the control of the arabinose-inducible $P_{araB}$ promoter. The pKD46 plasmid is necessary for integration of the PCR product into the chromosome of the MG1655 strain. The strain MG1655 can be obtained from American Type Culture Collection. (P.O. Box 1549 Manassas, Va. 20108, U.S.A.).

Electrocompetent cells were prepared as follows: *E. coli* MG1655/pKD46 cells were grown overnight at 30° C. in LB medium containing ampicillin (100 mg/l), and the culture was diluted 100 times with 5 ml of SOB medium (Sambrook et al, "Molecular Cloning: A Laboratory Manual, Second Edition", Cold Spring Harbor Laboratory Press, 1989) containing ampicillin and L-arabinose (1 mM). The cells were grown with aeration at 30° C. to an $OD_{600}$ of ≈0.6 and then were made electrocompetent by concentrating 100-fold and washing three times with ice-cold deionized $H_2O$. Electroporation was performed using 70 μl of cells and ≈100 ng of the PCR product. Cells after electroporation were incubated with 1 ml of SOC medium (Sambrook et al, "Molecular Cloning: A Laboratory Manual, Second Edition", Cold Spring Harbor Laboratory Press, 1989) at 37° C. for 2.5 hours and then were plated onto L-agar containing chloramphenicol (30 μg/ml) and grown at 37° C. to select $Cm^R$ recombinants. Then, to eliminate the pKD46 plasmid, two passages on L-agar with Cm at 42° C. were performed and the colonies were tested for sensitivity to ampicillin.

2. Verification of the artI Gene Deletion by PCR

Figure 2:
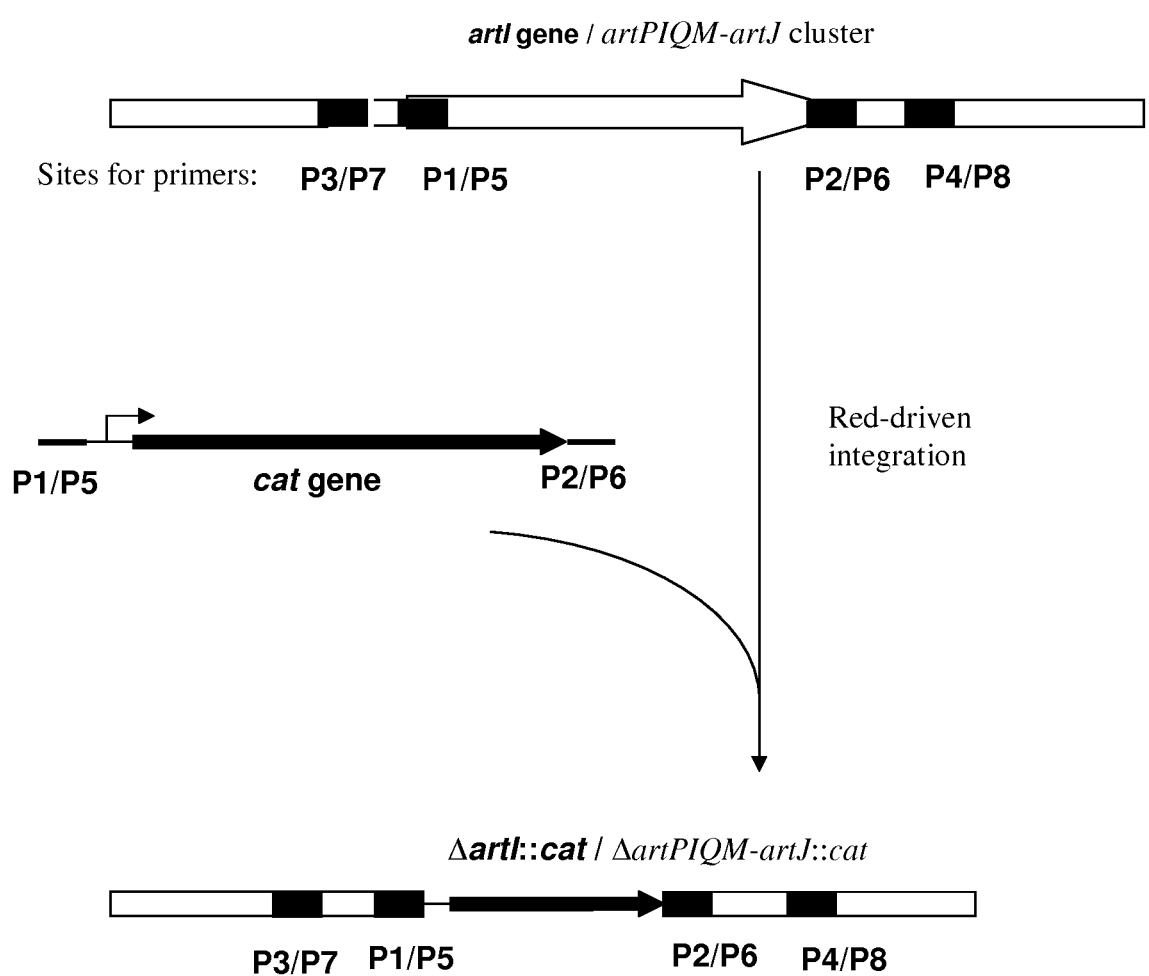
FIG. 2 shows the construction of the chromosomal DNA fragment comprising the inactivated artI gene or artPIQM-artJ cluster.

The mutants in which the artI gene had been deleted, and which were marked with Cm resistance gene, were verified by PCR using the locus-specific primers P3 (SEQ ID NO: 13) and P4 (SEQ ID NO: 14). For this purpose, a freshly isolated colony was suspended in 20 µl water and then 1 µl of the suspension was used for PCR. The temperature profile follows: initial DNA denaturation for 5 min at 95° C.; then 30 cycles of denaturation at 95° C. for 30 sec, annealing at 55° C. for 30 sec and elongation at 72° C. for 1 min; the final elongation for 5 min at 72° C. The PCR product obtained in the PCR reaction using the cells of the parental artI+ strain MG1655 as the template was 803 by in length. The PCR product obtained in the PCR reaction using the cells of the mutant MG1655 ΔartI::cat strain as the template was 1453 nucleotides in length (FIG. 2). The mutant strain was named MG1655ΔartI.

Example 2

Construction of a Strain with an Inactivated artPIQM-artJ Cluster

1. Deletion of the artPIQM-artJ Cluster

The artPIQM-artJ cluster in a bacterial strain was deleted by Red-driven integration. According to this procedure, the PCR primers P5 (SEQ ID NO: 15) and P6 (SEQ ID NO: 16), which are homologous to both the region adjacent to the artPIQM-artJ cluster and the gene which confers antibiotic resistance in the template plasmid, were constructed. The plasmid pMW118-attL-Cm-attR (WO 05/010175) was used as the template in the PCR reaction. Conditions for PCR were as described above.

The 1.7 kb PCR product (FIG. 1) was purified from an agarose gel and used for electroporation of the E. coli strain MG1655 (ATCC 700926), which contains the plasmid pKD46

Electrocompetent cells were prepared as described above. Electroporation was performed using 70 µl of cells and ≈100 ng of the PCR product. Cells after electroporation were incubated with 1 ml of SOC medium at 37° C. for 2.5 hours and then were plated onto L-agar containing chloramphenicol (30 µg/ml) and grown at 37° C. to select $Cm^R$ recombinants. Then, to eliminate the pKD46 plasmid, two passages on L-agar with Cm at 42° C. were performed and the colonies were tested for sensitivity to ampicillin.

2. Verification of Deletion of the artPIQM-artJ Cluster by PCR

The mutants in which the artPIQM-artJ cluster had been deleted, and which were marked with the Cm resistance gene, were verified by PCR using the locus-specific primers P7 (SEQ ID NO: 17) and P8 (SEQ ID NO: 18) as described above. The PCR product obtained in the PCR reaction using the cells of the mutant MG1655 ΔartPIQM-artJ::cat strain as the template was 1.5 kb nucleotides in length (FIG. 2)). The mutant strain was named MG1655ΔartPIMQ-artJ.

Example 3

Production of L-arginine by E. coli 382ΔartI and E. coli 382ΔartPIMQ-artJ.

To test the effect of inactivation of the artI gene or art-PIMQ-artJ cluster on L-arginine production, DNA fragments from the chromosome of the above-described E. coli MG1655ΔartI and E. coli MG1655ΔartPIMQ-artJ were transferred to the L-arginine producing E. coli strain 382 by P1 transduction (Miller, J. H. (1972) Experiments in Molecular Genetics, Cold Spring Harbor Lab. Press, Plainview, N.Y.) to obtain E. coli 382ΔartI and 382ΔartPIMQ-artJ strains, respectively. The strain 382 has been deposited in the Russian National Collection of Industrial Microorganisms (VKPM) (Russia, 117545 Moscow, 1 Dorozhny proezd, 1) on Apr. 10, 2000 under accession number VKPM B-7926 and then converted to a deposit under the Budapest Treaty on May 18, 2001.

The E. coli strains, 382, 382ΔartI and 382ΔartPIMQ-artJ, were separately cultivated with shaking at 37° C. for 18 hours in 3 ml of nutrient broth, and 0.3 ml of the cultures were inoculated into 2 ml of a fermentation medium in 20×200-mm test tubes and cultivated at 32° C. for 48 hours on a rotary shaker.

After the cultivation, the amount of L-arginine which has accumulated in the medium was determined by paper chromatography using the following mobile phase: butanol:acetic acid:water=4:1:1 (v/v). A solution of ninhydrin (2%) in acetone was used as a visualizing reagent. A spot containing L-arginine was cut out, the L-arginine was eluted with 0.5% water solution of $CdCl_2$, and the amount of L-arginine was estimated spectrophotometrically at 540 nm.

The composition of the fermentation medium (g/l) is as follows:

| | |
|---|---|
| Glucose | 48.0 |
| $(NH4)_2SO_4$ | 35.0 |
| $KH_2PO_4$ | 2.0 |
| $MgSO_4 \cdot 7H_2O$ | 1.0 |
| Thiamine HCl | 0.0002 |
| Yeast extract | 1.0 |
| L-isoleucine | 0.1 |
| $CaCO_3$ | 5.0 |

Glucose and magnesium sulfate are sterilized separately. $CaCO_3$ is dry-heat sterilized at 180 C for 2 hours. The pH is adjusted to 7.0.

The results of test tube fermentations are shown in Table 1. As it can be seen from the Table 1, strains with inactivated artI gene or artPIMQ-artJ cluster caused a higher amount of accumulation of L-arginine as compared with parent L-arginine producing E. coli strain 382.

TABLE 1

| Strain | Amount of L-arginine, g/l |
|---|---|
| 382 | 12.0 ± 0.1 |
| 382ΔartI | 14.3 ± 0.1 |
| 382ΔartPIMQ-artJ | 13.4 ± 0.1 |

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

What is claimed is:

1. A method for producing L-arginine comprising:
cultivating an L-arginine producing *Escherichia coli* bacterium in a medium, and
collecting L-arginine from the medium, wherein said bacterium has a modification consisting of inactivation of an artI gene;
wherein said artI gene encodes a protein having a homology of not less than 95% with respect to the entire amino acid sequence of SEQ ID NO: 4, wherein said inactivation results in increased production of L-arginine.

* * * * *

SEQUENCE LISTING

<160> NUMBER OF SEQ ID NOS: 18

<210> SEQ ID NO 1
<211> LENGTH: 729
<212> TYPE: DNA
<213> ORGANISM: Escherichia coli
<220> FEATURE:
<221> NAME/KEY: CDS
<222> LOCATION: (1)..(729)

<400> SEQUENCE: 1

```
atg agt att caa tta aac ggc att aat tgc ttc tac ggc gcg cat cag      48
Met Ser Ile Gln Leu Asn Gly Ile Asn Cys Phe Tyr Gly Ala His Gln
1               5                   10                  15 gcg ctg ttc gat atc acg ctg gat tgc cca cag ggc gaa acg ctg gtg      96
Ala Leu Phe Asp Ile Thr Leu Asp Cys Pro Gln Gly Glu Thr Leu Val
            20                  25                  30 tta ctt ggc ccc agc ggc gcg ggt aaa agc tcg ctg ctg cgt gta ctc     144
Leu Leu Gly Pro Ser Gly Ala Gly Lys Ser Ser Leu Leu Arg Val Leu
        35                  40                  45 aat ctg ctt gag atg ccg cgc tcc ggt acg ctc aac att gca ggc aac     192
Asn Leu Leu Glu Met Pro Arg Ser Gly Thr Leu Asn Ile Ala Gly Asn
    50                  55                  60 cat ttc gat ttc acc aaa aca ccc tct gac aaa gcg att cgc gat ttg     240
His Phe Asp Phe Thr Lys Thr Pro Ser Asp Lys Ala Ile Arg Asp Leu
65                  70                  75                  80 cgt cgt aac gtt ggc atg gtg ttt cag caa tac aac ctg tgg ccg cat     288
Arg Arg Asn Val Gly Met Val Phe Gln Gln Tyr Asn Leu Trp Pro His
                85                  90                  95 ctg acc gtg cag caa aac ctg att gaa gcg ccc tgc cgt gta ctg ggg     336
Leu Thr Val Gln Gln Asn Leu Ile Glu Ala Pro Cys Arg Val Leu Gly
            100                 105                 110 ttg agt aaa gat cag gcg ctg gcc cgt gca gaa aaa ctg ctg gaa cgt     384
Leu Ser Lys Asp Gln Ala Leu Ala Arg Ala Glu Lys Leu Leu Glu Arg
        115                 120                 125 ctg cgt ctc aaa cct tat agc gat cgt tac ccg ctg cat ctt tct ggt     432
Leu Arg Leu Lys Pro Tyr Ser Asp Arg Tyr Pro Leu His Leu Ser Gly
    130                 135                 140 ggt cag cag cag cgt gtt gct att gcc cgt gcg ttg atg atg gaa ccg     480
Gly Gln Gln Gln Arg Val Ala Ile Ala Arg Ala Leu Met Met Glu Pro
145                 150                 155                 160 cag gta ctg ctg ttc gat gaa ccg acc gcc gca ctg gac ccg gaa att     528
Gln Val Leu Leu Phe Asp Glu Pro Thr Ala Ala Leu Asp Pro Glu Ile
                165                 170                 175 acg gca caa atc gtc agc atc att cgt gag ctg gca gaa acg aat att     576
Thr Ala Gln Ile Val Ser Ile Ile Arg Glu Leu Ala Glu Thr Asn Ile
            180                 185                 190 acc cag gtg atc gtc acc cac gaa gtt gaa gtg gcg cgt aaa acc gcc     624
Thr Gln Val Ile Val Thr His Glu Val Glu Val Ala Arg Lys Thr Ala
        195                 200                 205 agc cga gtg gtg tat atg gaa aat ggt cat atc gta gaa caa ggc gac     672
Ser Arg Val Val Tyr Met Glu Asn Gly His Ile Val Glu Gln Gly Asp
    210                 215                 220 gcg agc tgc ttt acc gag ccg caa acc gaa gca ttt aaa aac tat ctc     720
Ala Ser Cys Phe Thr Glu Pro Gln Thr Glu Ala Phe Lys Asn Tyr Leu
225                 230                 235                 240 tct cac taa                                                         729
Ser His
```

<210> SEQ ID NO 2

```
<211> LENGTH: 242
<212> TYPE: PRT
<213> ORGANISM: Escherichia coli

<400> SEQUENCE: 2

Met Ser Ile Gln Leu Asn Gly Ile Asn Cys Phe Tyr Gly Ala His Gln
1               5                   10                  15

Ala Leu Phe Asp Ile Thr Leu Asp Cys Pro Gln Gly Glu Thr Leu Val
            20                  25                  30

Leu Leu Gly Pro Ser Gly Ala Gly Lys Ser Ser Leu Leu Arg Val Leu
        35                  40                  45

Asn Leu Leu Glu Met Pro Arg Ser Gly Thr Leu Asn Ile Ala Gly Asn
50                  55                  60

His Phe Asp Phe Thr Lys Thr Pro Ser Asp Lys Ala Ile Arg Asp Leu
65                  70                  75                  80

Arg Arg Asn Val Gly Met Val Phe Gln Gln Tyr Asn Leu Trp Pro His
                85                  90                  95

Leu Thr Val Gln Gln Asn Leu Ile Glu Ala Pro Cys Arg Val Leu Gly
            100                 105                 110

Leu Ser Lys Asp Gln Ala Leu Ala Arg Ala Glu Lys Leu Leu Glu Arg
        115                 120                 125

Leu Arg Leu Lys Pro Tyr Ser Asp Arg Tyr Pro Leu His Leu Ser Gly
130                 135                 140

Gly Gln Gln Gln Arg Val Ala Ile Ala Arg Ala Leu Met Met Glu Pro
145                 150                 155                 160

Gln Val Leu Leu Phe Asp Glu Pro Thr Ala Ala Leu Asp Pro Glu Ile
                165                 170                 175

Thr Ala Gln Ile Val Ser Ile Ile Arg Glu Leu Ala Glu Thr Asn Ile
            180                 185                 190

Thr Gln Val Ile Val Thr His Glu Val Glu Val Ala Arg Lys Thr Ala
        195                 200                 205

Ser Arg Val Val Tyr Met Glu Asn Gly His Ile Val Glu Gln Gly Asp
210                 215                 220

Ala Ser Cys Phe Thr Glu Pro Gln Thr Glu Ala Phe Lys Asn Tyr Leu
225                 230                 235                 240

Ser His

<210> SEQ ID NO 3
<211> LENGTH: 732
<212> TYPE: DNA
<213> ORGANISM: Escherichia coli
<220> FEATURE:
<221> NAME/KEY: CDS
<222> LOCATION: (1)..(732)

<400> SEQUENCE: 3 atg aaa aaa gtt ctg att gcc gcg tta att gca ggt ttt agt ctt tcc     48
Met Lys Lys Val Leu Ile Ala Ala Leu Ile Ala Gly Phe Ser Leu Ser
1               5                   10                  15 gcc aca gct gcc gaa acc att cgt ttt gct acc gaa gcc tcc tat cct     96
Ala Thr Ala Ala Glu Thr Ile Arg Phe Ala Thr Glu Ala Ser Tyr Pro
            20                  25                  30 ccg ttt gaa tcg att gat gca aac aac cag atc gtt ggt ttt gac gtc    144
Pro Phe Glu Ser Ile Asp Ala Asn Asn Gln Ile Val Gly Phe Asp Val
        35                  40                  45 gac ctg gca caa gcg ctg tgt aaa gag att gat gca acc tgc act ttc    192
Asp Leu Ala Gln Ala Leu Cys Lys Glu Ile Asp Ala Thr Cys Thr Phe
50                  55                  60
```

```
tct aac cag gcg ttt gac agc ctg atc cca agc ctg aaa ttc cgt cgc      240
Ser Asn Gln Ala Phe Asp Ser Leu Ile Pro Ser Leu Lys Phe Arg Arg
 65              70                  75                  80 gta gaa gcc gtg atg gcg ggc atg gat atc act ccg gag cgt gaa aag      288
Val Glu Ala Val Met Ala Gly Met Asp Ile Thr Pro Glu Arg Glu Lys
             85                  90                  95 cag gtg ctg ttt acc acc ccg tac tat gac aac tct gcc ctg ttt gtg      336
Gln Val Leu Phe Thr Thr Pro Tyr Tyr Asp Asn Ser Ala Leu Phe Val
            100                 105                 110 ggt cag caa ggc aaa tac acc agt gtt gat cag ctg aaa ggc aaa aaa      384
Gly Gln Gln Gly Lys Tyr Thr Ser Val Asp Gln Leu Lys Gly Lys Lys
        115                 120                 125 gtc ggc gta cag aac ggg acg aca cac cag aaa ttc att atg gat aag      432
Val Gly Val Gln Asn Gly Thr Thr His Gln Lys Phe Ile Met Asp Lys
    130                 135                 140 cac ccg gaa atc act acc gtt ccg tat gac agc tac cag aac gca aaa      480
His Pro Glu Ile Thr Thr Val Pro Tyr Asp Ser Tyr Gln Asn Ala Lys
145                 150                 155                 160 ctg gat ctg caa aac ggg cgt atc gac ggc gtc ttc ggt gac acc gca      528
Leu Asp Leu Gln Asn Gly Arg Ile Asp Gly Val Phe Gly Asp Thr Ala
                165                 170                 175 gtg gtc act gag tgg ctg aaa gat aac ccg aaa ctg gcg gcg gtg ggc      576
Val Val Thr Glu Trp Leu Lys Asp Asn Pro Lys Leu Ala Ala Val Gly
            180                 185                 190 gac aaa gtg acc gat aaa gat tac ttc ggc act ggc ctc ggc atc gcg      624
Asp Lys Val Thr Asp Lys Asp Tyr Phe Gly Thr Gly Leu Gly Ile Ala
        195                 200                 205 gta cgt cag ggc aac act gag ctg cag cag aaa ctc aac act gcg ctg      672
Val Arg Gln Gly Asn Thr Glu Leu Gln Gln Lys Leu Asn Thr Ala Leu
    210                 215                 220 gaa aaa gtg aag aaa gat ggc act tac gaa acc atc tac aac aaa tgg      720
Glu Lys Val Lys Lys Asp Gly Thr Tyr Glu Thr Ile Tyr Asn Lys Trp
225                 230                 235                 240 ttc cag aag taa                                                       732
Phe Gln Lys <210> SEQ ID NO 4
<211> LENGTH: 243
<212> TYPE: PRT
<213> ORGANISM: Escherichia coli

<400> SEQUENCE: 4

Met Lys Lys Val Leu Ile Ala Ala Leu Ile Ala Gly Phe Ser Leu Ser
1               5                   10                  15

Ala Thr Ala Ala Glu Thr Ile Arg Phe Ala Thr Glu Ala Ser Tyr Pro
            20                  25                  30

Pro Phe Glu Ser Ile Asp Ala Asn Asn Gln Ile Val Gly Phe Asp Val
        35                  40                  45

Asp Leu Ala Gln Ala Leu Cys Lys Glu Ile Asp Ala Thr Cys Thr Phe
    50                  55                  60

Ser Asn Gln Ala Phe Asp Ser Leu Ile Pro Ser Leu Lys Phe Arg Arg
65                  70                  75                  80

Val Glu Ala Val Met Ala Gly Met Asp Ile Thr Pro Glu Arg Glu Lys
                85                  90                  95

Gln Val Leu Phe Thr Thr Pro Tyr Tyr Asp Asn Ser Ala Leu Phe Val
            100                 105                 110

Gly Gln Gln Gly Lys Tyr Thr Ser Val Asp Gln Leu Lys Gly Lys Lys
        115                 120                 125

Val Gly Val Gln Asn Gly Thr Thr His Gln Lys Phe Ile Met Asp Lys
```

```
                    130                 135                 140
His Pro Glu Ile Thr Thr Val Pro Tyr Asp Ser Tyr Gln Asn Ala Lys
145                 150                 155                 160

Leu Asp Leu Gln Asn Gly Arg Ile Asp Gly Val Phe Gly Asp Thr Ala
                165                 170                 175

Val Val Thr Glu Trp Leu Lys Asp Asn Pro Lys Leu Ala Ala Val Gly
            180                 185                 190

Asp Lys Val Thr Asp Lys Asp Tyr Phe Gly Thr Gly Leu Gly Ile Ala
                195                 200                 205

Val Arg Gln Gly Asn Thr Glu Leu Gln Gln Lys Leu Asn Thr Ala Leu
            210                 215                 220

Glu Lys Val Lys Lys Asp Gly Thr Tyr Glu Thr Ile Tyr Asn Lys Trp
225                 230                 235                 240

Phe Gln Lys

<210> SEQ ID NO 5
<211> LENGTH: 717
<212> TYPE: DNA
<213> ORGANISM: Escherichia coli
<220> FEATURE:
<221> NAME/KEY: CDS
<222> LOCATION: (1)..(717)

<400> SEQUENCE: 5 atg aat gaa ttt ttt cct tta gca agc gcc gcc ggg atg acc gtc ggc      48
Met Asn Glu Phe Phe Pro Leu Ala Ser Ala Ala Gly Met Thr Val Gly
1               5                   10                  15 ctt gcc gtt tgt gca ttg att gtc ggg ctg gcg ctg gcg atg ttc ttt      96
Leu Ala Val Cys Ala Leu Ile Val Gly Leu Ala Leu Ala Met Phe Phe
            20                  25                  30 gcg gta tgg gag tcg gca aaa tgg cgt cct gtc gcg tgg gca ggt tca     144
Ala Val Trp Glu Ser Ala Lys Trp Arg Pro Val Ala Trp Ala Gly Ser
        35                  40                  45 gcg ctg gta acc att ctg cgt ggc ctg cca gaa att ctg gtg gtg ctg     192
Ala Leu Val Thr Ile Leu Arg Gly Leu Pro Glu Ile Leu Val Val Leu
    50                  55                  60 ttt atc tat ttt ggc tcc tcg cag ctg ctg ctg acg ctt tcg gat ggc     240
Phe Ile Tyr Phe Gly Ser Ser Gln Leu Leu Leu Thr Leu Ser Asp Gly
65                  70                  75                  80 ttc act atc aat ctt ggg ttc gtg cag atc cca gtg cag atg gac att     288
Phe Thr Ile Asn Leu Gly Phe Val Gln Ile Pro Val Gln Met Asp Ile
                85                  90                  95 gag aac ttc gac gtt agc ccg ttc ctt tgt ggt gtc atc gct ctg tca     336
Glu Asn Phe Asp Val Ser Pro Phe Leu Cys Gly Val Ile Ala Leu Ser
            100                 105                 110 ctg ctg tat gcc gcc tat gcc tcg caa acg ctt cgg ggc gcg ttg aaa     384
Leu Leu Tyr Ala Ala Tyr Ala Ser Gln Thr Leu Arg Gly Ala Leu Lys
        115                 120                 125 gcg gtg ccg gtg ggt cag tgg gag tct ggt cag gcg ctg ggg ctg tcg     432
Ala Val Pro Val Gly Gln Trp Glu Ser Gly Gln Ala Leu Gly Leu Ser
    130                 135                 140 aaa tcg gct atc ttt ttc cgt ctg gtg atg ccg cag atg tgg cgt cat     480
Lys Ser Ala Ile Phe Phe Arg Leu Val Met Pro Gln Met Trp Arg His
145                 150                 155                 160 gcg ctg cct ggc ctc ggt aac cag tgg ctg gtg ctg aaa gat acc         528
Ala Leu Pro Gly Leu Gly Asn Gln Trp Leu Val Leu Lys Asp Thr
                165                 170                 175 gcg ctg gtc agt ttg att agt gtg aat gat tta atg ctg caa aca aaa     576
Ala Leu Val Ser Leu Ile Ser Val Asn Asp Leu Met Leu Gln Thr Lys
            180                 185                 190
```

| | | | | | | | | | | | | | | | |
|---|---|---|---|---|---|---|---|---|---|---|---|---|---|---|---|
| agc | atc | gct | act | cgt | acc | cag | gaa | cca | ttt | acc | tgg | tac | att | gtg | gcg |
| Ser | Ile | Ala | Thr | Arg | Thr | Gln | Glu | Pro | Phe | Thr | Trp | Tyr | Ile | Val | Ala |
| | | 195 | | | | 200 | | | | | 205 | | | | |

624

| gcg | gcg | att | tac | ctg | gtg | atc | acc | ctg | ctc | agt | cag | tac | att | ctc | aaa |
|---|---|---|---|---|---|---|---|---|---|---|---|---|---|---|---|
| Ala | Ala | Ile | Tyr | Leu | Val | Ile | Thr | Leu | Leu | Ser | Gln | Tyr | Ile | Leu | Lys |
| | 210 | | | | | 215 | | | | | 220 | | | | |

672

| cgc | att | gac | ctg | cgc | gcg | aca | cgt | ttt | gag | cgg | agg | ccc | agc | taa |
|---|---|---|---|---|---|---|---|---|---|---|---|---|---|---|
| Arg | Ile | Asp | Leu | Arg | Ala | Thr | Arg | Phe | Glu | Arg | Arg | Pro | Ser | |
| 225 | | | | | 230 | | | | | 235 | | | | |

717

<210> SEQ ID NO 6
<211> LENGTH: 238
<212> TYPE: PRT
<213> ORGANISM: Escherichia coli

<400> SEQUENCE: 6

Met Asn Glu Phe Phe Pro Leu Ala Ser Ala Gly Met Thr Val Gly
1               5                   10                  15

Leu Ala Val Cys Ala Leu Ile Val Gly Leu Ala Leu Ala Met Phe Phe
            20                  25                  30

Ala Val Trp Glu Ser Ala Lys Trp Arg Pro Val Ala Trp Ala Gly Ser
        35                  40                  45

Ala Leu Val Thr Ile Leu Arg Gly Leu Pro Glu Ile Leu Val Val Leu
    50                  55                  60

Phe Ile Tyr Phe Gly Ser Ser Gln Leu Leu Leu Thr Leu Ser Asp Gly
65                  70                  75                  80

Phe Thr Ile Asn Leu Gly Phe Val Gln Ile Pro Val Gln Met Asp Ile
                85                  90                  95

Glu Asn Phe Asp Val Ser Pro Phe Leu Cys Gly Val Ile Ala Leu Ser
            100                 105                 110

Leu Leu Tyr Ala Ala Tyr Ala Ser Gln Thr Leu Arg Gly Ala Leu Lys
        115                 120                 125

Ala Val Pro Val Gly Gln Trp Glu Ser Gly Gln Ala Leu Gly Leu Ser
    130                 135                 140

Lys Ser Ala Ile Phe Phe Arg Leu Val Met Pro Gln Met Trp Arg His
145                 150                 155                 160

Ala Leu Pro Gly Leu Gly Asn Gln Trp Leu Val Leu Leu Lys Asp Thr
                165                 170                 175

Ala Leu Val Ser Leu Ile Ser Val Asn Asp Leu Met Leu Gln Thr Lys
            180                 185                 190

Ser Ile Ala Thr Arg Thr Gln Glu Pro Phe Thr Trp Tyr Ile Val Ala
        195                 200                 205

Ala Ala Ile Tyr Leu Val Ile Thr Leu Leu Ser Gln Tyr Ile Leu Lys
    210                 215                 220

Arg Ile Asp Leu Arg Ala Thr Arg Phe Glu Arg Arg Pro Ser
225                 230                 235

<210> SEQ ID NO 7
<211> LENGTH: 669
<212> TYPE: DNA
<213> ORGANISM: Escherichia coli
<220> FEATURE:
<221> NAME/KEY: CDS
<222> LOCATION: (1)..(669)

<400> SEQUENCE: 7

| | | | | | | | | | | | | | | | |
|---|---|---|---|---|---|---|---|---|---|---|---|---|---|---|---|
| atg | ttt | gag | tat | tta | ccc | gaa | ctg | atg | aaa | ggg | cta | cac | acc | agc | ctg |
| Met | Phe | Glu | Tyr | Leu | Pro | Glu | Leu | Met | Lys | Gly | Leu | His | Thr | Ser | Leu |
| 1 | | | | 5 | | | | | 10 | | | | | 15 | |

48

```
acg cta acc gtt gcc tcg ctg att gtg gca ctg att ctg gca ttg att    96
Thr Leu Thr Val Ala Ser Leu Ile Val Ala Leu Ile Leu Ala Leu Ile
         20                  25                  30 ttt acc atc atc ctg acg ctg aaa acg ccg gtg ctg gtg tgg ctg gtg   144
Phe Thr Ile Ile Leu Thr Leu Lys Thr Pro Val Leu Val Trp Leu Val
         35                  40                  45 cgg ggt tat atc acg ctg ttt acc ggt acg ccg ctg ctg gtg cag atc   192
Arg Gly Tyr Ile Thr Leu Phe Thr Gly Thr Pro Leu Leu Val Gln Ile
 50                  55                  60 ttc ctg att tat tac ggg ccg ggc cag ttt ccg act ttg cag gag tat   240
Phe Leu Ile Tyr Tyr Gly Pro Gly Gln Phe Pro Thr Leu Gln Glu Tyr
 65                  70                  75                  80 ccg gca ctg tgg cat ttg ttg tca gaa ccg tgg tta tgt gcg ctg att   288
Pro Ala Leu Trp His Leu Leu Ser Glu Pro Trp Leu Cys Ala Leu Ile
                 85                  90                  95 gcg ttg tcg ctg aat agt gcg gcg tat acc acg cag ctg ttt tac ggt   336
Ala Leu Ser Leu Asn Ser Ala Ala Tyr Thr Thr Gln Leu Phe Tyr Gly
                100                 105                 110 gca att cgt gcg atc ccg gaa ggt cag tgg cag tcc tgt agc gcc ctg   384
Ala Ile Arg Ala Ile Pro Glu Gly Gln Trp Gln Ser Cys Ser Ala Leu
            115                 120                 125 gga atg agc aaa aaa gat acg ctg gcg atc ctg ctg ccg tat gcc ttt   432
Gly Met Ser Lys Lys Asp Thr Leu Ala Ile Leu Leu Pro Tyr Ala Phe
130                 135                 140 aaa cgc tcg ctc tct tct tat tcc aac gaa gtg gtg ctg gta ttc aaa   480
Lys Arg Ser Leu Ser Ser Tyr Ser Asn Glu Val Val Leu Val Phe Lys
145                 150                 155                 160 agt acc tct ctg gca tac acc att acg ctg atg gaa gtg atg gga tac   528
Ser Thr Ser Leu Ala Tyr Thr Ile Thr Leu Met Glu Val Met Gly Tyr
                165                 170                 175 agc cag ttg ttg tac gga cgc acc tac gat gta atg gtg ttc ggt gcg   576
Ser Gln Leu Leu Tyr Gly Arg Thr Tyr Asp Val Met Val Phe Gly Ala
            180                 185                 190 gca ggg att att tac ctg gtc gtt aac ggc ctg ctg acg ctg atg atg   624
Ala Gly Ile Ile Tyr Leu Val Val Asn Gly Leu Leu Thr Leu Met Met
        195                 200                 205 cgt ctg atc gag cgc aaa gcg ctg gca ttc gaa cgg cga aat taa       669
Arg Leu Ile Glu Arg Lys Ala Leu Ala Phe Glu Arg Arg Asn
210                 215                 220
```

<210> SEQ ID NO 8
<211> LENGTH: 222
<212> TYPE: PRT
<213> ORGANISM: Escherichia coli

<400> SEQUENCE: 8

```
Met Phe Glu Tyr Leu Pro Glu Leu Met Lys Gly Leu His Thr Ser Leu
 1               5                  10                  15

Thr Leu Thr Val Ala Ser Leu Ile Val Ala Leu Ile Leu Ala Leu Ile
            20                  25                  30

Phe Thr Ile Ile Leu Thr Leu Lys Thr Pro Val Leu Val Trp Leu Val
        35                  40                  45

Arg Gly Tyr Ile Thr Leu Phe Thr Gly Thr Pro Leu Leu Val Gln Ile
 50                  55                  60

Phe Leu Ile Tyr Tyr Gly Pro Gly Gln Phe Pro Thr Leu Gln Glu Tyr
 65                  70                  75                  80

Pro Ala Leu Trp His Leu Leu Ser Glu Pro Trp Leu Cys Ala Leu Ile
                 85                  90                  95

Ala Leu Ser Leu Asn Ser Ala Ala Tyr Thr Thr Gln Leu Phe Tyr Gly
```

-continued

```
                    100                 105                 110
Ala Ile Arg Ala Ile Pro Glu Gly Gln Trp Gln Ser Cys Ser Ala Leu
            115                 120                 125

Gly Met Ser Lys Lys Asp Thr Leu Ala Ile Leu Leu Pro Tyr Ala Phe
        130                 135                 140

Lys Arg Ser Leu Ser Ser Tyr Ser Asn Glu Val Val Leu Val Phe Lys
145                 150                 155                 160

Ser Thr Ser Leu Ala Tyr Thr Ile Thr Leu Met Glu Val Met Gly Tyr
                165                 170                 175

Ser Gln Leu Leu Tyr Gly Arg Thr Tyr Asp Val Met Val Phe Gly Ala
            180                 185                 190

Ala Gly Ile Ile Tyr Leu Val Val Asn Gly Leu Leu Thr Leu Met Met
        195                 200                 205

Arg Leu Ile Glu Arg Lys Ala Leu Ala Phe Glu Arg Arg Asn
210                 215                 220

<210> SEQ ID NO 9
<211> LENGTH: 732
<212> TYPE: DNA
<213> ORGANISM: Escherichia coli
<220> FEATURE:
<221> NAME/KEY: CDS
<222> LOCATION: (1)..(732)

<400> SEQUENCE: 9
```

| | | | | | | | | | | | | | | | | |
|---|---|---|---|---|---|---|---|---|---|---|---|---|---|---|---|---|
| atg | aaa | aag | tta | gtt | ctt | gcc | gct | tta | ctt | gct | tcc | ttt | act | ttc | ggt | 48 |
| Met | Lys | Lys | Leu | Val | Leu | Ala | Ala | Leu | Leu | Ala | Ser | Phe | Thr | Phe | Gly | |
| 1 | | | | 5 | | | | | 10 | | | | | 15 | | |
| gct | tct | gcc | gca | gag | aaa | atc | aat | ttt | ggc | gtt | tca | gcc | acc | tat | cca | 96 |
| Ala | Ser | Ala | Ala | Glu | Lys | Ile | Asn | Phe | Gly | Val | Ser | Ala | Thr | Tyr | Pro | |
| | | | 20 | | | | | 25 | | | | | 30 | | | |
| ccc | ttt | gaa | tct | ata | ggt | gct | aat | aat | gag | att | gtc | ggc | ttt | gat | atc | 144 |
| Pro | Phe | Glu | Ser | Ile | Gly | Ala | Asn | Asn | Glu | Ile | Val | Gly | Phe | Asp | Ile | |
| | | 35 | | | | | 40 | | | | | 45 | | | | |
| gat | ctg | gca | aaa | gcc | ttg | tgc | aaa | caa | atg | cag | gca | gaa | tgt | act | ttt | 192 |
| Asp | Leu | Ala | Lys | Ala | Leu | Cys | Lys | Gln | Met | Gln | Ala | Glu | Cys | Thr | Phe | |
| | 50 | | | | | 55 | | | | | 60 | | | | | |
| act | aat | cac | gcg | ttc | gac | agc | ctg | atc | ccg | tcc | ctg | aaa | ttc | aga | aaa | 240 |
| Thr | Asn | His | Ala | Phe | Asp | Ser | Leu | Ile | Pro | Ser | Leu | Lys | Phe | Arg | Lys | |
| 65 | | | | | 70 | | | | | 75 | | | | | 80 | |
| tat | gac | gcc | gta | atc | tcc | ggt | atg | gat | atc | acc | ccg | gag | cgt | agc | aaa | 288 |
| Tyr | Asp | Ala | Val | Ile | Ser | Gly | Met | Asp | Ile | Thr | Pro | Glu | Arg | Ser | Lys | |
| | | | | 85 | | | | | 90 | | | | | 95 | | |
| cag | gta | tcg | ttt | acc | acg | ccc | tac | tat | gaa | aac | tca | gcc | gtc | gtg | att | 336 |
| Gln | Val | Ser | Phe | Thr | Thr | Pro | Tyr | Tyr | Glu | Asn | Ser | Ala | Val | Val | Ile | |
| | | | 100 | | | | | 105 | | | | | 110 | | | |
| gcc | aaa | aaa | gat | acc | tac | aaa | acg | ttt | gcc | gat | ctg | aaa | ggc | aaa | cgt | 384 |
| Ala | Lys | Lys | Asp | Thr | Tyr | Lys | Thr | Phe | Ala | Asp | Leu | Lys | Gly | Lys | Arg | |
| | | 115 | | | | | 120 | | | | | 125 | | | | |
| att | ggg | atg | gaa | aac | ggt | act | acg | cac | cag | aaa | tat | att | cag | gat | cag | 432 |
| Ile | Gly | Met | Glu | Asn | Gly | Thr | Thr | His | Gln | Lys | Tyr | Ile | Gln | Asp | Gln | |
| | 130 | | | | | 135 | | | | | 140 | | | | | |
| cac | ccg | gaa | gtg | aaa | act | gtc | tct | tat | gac | agt | tat | cag | aat | gcc | ttt | 480 |
| His | Pro | Glu | Val | Lys | Thr | Val | Ser | Tyr | Asp | Ser | Tyr | Gln | Asn | Ala | Phe | |
| 145 | | | | | 150 | | | | | 155 | | | | | 160 | |
| atc | gat | ctg | aaa | aat | ggt | cgt | att | gat | ggg | gta | ttt | ggt | gac | aca | gcg | 528 |
| Ile | Asp | Leu | Lys | Asn | Gly | Arg | Ile | Asp | Gly | Val | Phe | Gly | Asp | Thr | Ala | |
| | | | | 165 | | | | | 170 | | | | | 175 | | |
| gtg | gta | aac | gaa | tgg | ctg | aaa | acc | aat | cca | caa | ctt | ggt | gtt | gct | act | 576 |
| Val | Val | Asn | Glu | Trp | Leu | Lys | Thr | Asn | Pro | Gln | Leu | Gly | Val | Ala | Thr | |

```
                    180                 185                 190
gag aaa gtg acc gat ccg caa tat ttt ggc acc ggc ctg ggc atc gct      624
Glu Lys Val Thr Asp Pro Gln Tyr Phe Gly Thr Gly Leu Gly Ile Ala
        195                 200                 205 gta cgt ccg gat aac aaa gcc ctg ctg gaa aaa ctg aat aac gcg ctg      672
Val Arg Pro Asp Asn Lys Ala Leu Leu Glu Lys Leu Asn Asn Ala Leu
210                 215                 220 gca gca att aaa gct gac ggt act tat caa aaa atc agt gac cag tgg      720
Ala Ala Ile Lys Ala Asp Gly Thr Tyr Gln Lys Ile Ser Asp Gln Trp
225                 230                 235                 240 ttc cca cag taa                                                      732
Phe Pro Gln <210> SEQ ID NO 10
<211> LENGTH: 243
<212> TYPE: PRT
<213> ORGANISM: Escherichia coli

<400> SEQUENCE: 10

Met Lys Lys Leu Val Leu Ala Ala Leu Leu Ala Ser Phe Thr Phe Gly
1               5                   10                  15

Ala Ser Ala Ala Glu Lys Ile Asn Phe Gly Val Ser Ala Thr Tyr Pro
                20                  25                  30

Pro Phe Glu Ser Ile Gly Ala Asn Asn Glu Ile Val Gly Phe Asp Ile
            35                  40                  45

Asp Leu Ala Lys Ala Leu Cys Lys Gln Met Gln Ala Glu Cys Thr Phe
        50                  55                  60

Thr Asn His Ala Phe Asp Ser Leu Ile Pro Ser Leu Lys Phe Arg Lys
65                  70                  75                  80

Tyr Asp Ala Val Ile Ser Gly Met Asp Ile Thr Pro Glu Arg Ser Lys
                85                  90                  95

Gln Val Ser Phe Thr Thr Pro Tyr Tyr Glu Asn Ser Ala Val Val Ile
            100                 105                 110

Ala Lys Lys Asp Thr Tyr Lys Thr Phe Ala Asp Leu Lys Gly Lys Arg
        115                 120                 125

Ile Gly Met Glu Asn Gly Thr Thr His Gln Lys Tyr Ile Gln Asp Gln
130                 135                 140

His Pro Glu Val Lys Thr Val Ser Tyr Asp Ser Tyr Gln Asn Ala Phe
145                 150                 155                 160

Ile Asp Leu Lys Asn Gly Arg Ile Asp Gly Val Phe Gly Asp Thr Ala
                165                 170                 175

Val Val Asn Glu Trp Leu Lys Thr Asn Pro Gln Leu Gly Val Ala Thr
            180                 185                 190

Glu Lys Val Thr Asp Pro Gln Tyr Phe Gly Thr Gly Leu Gly Ile Ala
        195                 200                 205

Val Arg Pro Asp Asn Lys Ala Leu Leu Glu Lys Leu Asn Asn Ala Leu
210                 215                 220

Ala Ala Ile Lys Ala Asp Gly Thr Tyr Gln Lys Ile Ser Asp Gln Trp
225                 230                 235                 240

Phe Pro Gln

<210> SEQ ID NO 11
<211> LENGTH: 64
<212> TYPE: DNA
<213> ORGANISM: Artificial sequence
<220> FEATURE:
<223> OTHER INFORMATION: primer
```

-continued

<400> SEQUENCE: 11
aaaaagttct gattgccgcg ttaattgcag gttttacgct caagttagta taaaaaagct    60
gaac                                                                 64

<210> SEQ ID NO 12
<211> LENGTH: 64
<212> TYPE: DNA
<213> ORGANISM: Artificial sequence
<220> FEATURE:
<223> OTHER INFORMATION: primer

<400> SEQUENCE: 12
gtttcgtaag tgccatcttt cttcactttt tccagctgaa gcctgctttt ttatactaag    60
ttgg                                                                 64

<210> SEQ ID NO 13
<211> LENGTH: 22
<212> TYPE: DNA
<213> ORGANISM: Artificial sequence
<220> FEATURE:
<223> OTHER INFORMATION: primer

<400> SEQUENCE: 13
atgaaaaaag ttctgattgc cg                                             22

<210> SEQ ID NO 14
<211> LENGTH: 20
<212> TYPE: DNA
<213> ORGANISM: Artificial sequence
<220> FEATURE:
<223> OTHER INFORMATION: primer

<400> SEQUENCE: 14
aatgcacaaa cggcaaggcc                                                20

<210> SEQ ID NO 15
<211> LENGTH: 64
<212> TYPE: DNA
<213> ORGANISM: Artificial sequence
<220> FEATURE:
<223> OTHER INFORMATION: primer

<400> SEQUENCE: 15
tagctatcag actgccagta tacgagtgtc aatgagcgct caagttagta taaaaaagct    60
gaac                                                                 64

<210> SEQ ID NO 16
<211> LENGTH: 64
<212> TYPE: DNA
<213> ORGANISM: Artificial sequence
<220> FEATURE:
<223> OTHER INFORMATION: primer

<400> SEQUENCE: 16
tctcaagccg cggttgcggc tttctgaatc ttactgtgaa gcctgccttt ttatactaag    60
ttgg                                                                 64

<210> SEQ ID NO 17
<211> LENGTH: 20
<212> TYPE: DNA
<213> ORGANISM: Artificial sequence
<220> FEATURE:
<223> OTHER INFORMATION: primer

```
<400> SEQUENCE: 17
gacatttatg ctcgccgacc                                          20

<210> SEQ ID NO 18
<211> LENGTH: 20
<212> TYPE: DNA
<213> ORGANISM: Artificial sequence
<220> FEATURE:
<223> OTHER INFORMATION: primer

<400> SEQUENCE: 18
aggcctgata agcgtagcgc                                          20
```